(12) United States Patent
Kobayashi

(10) Patent No.: US 9,320,483 B2
(45) Date of Patent: Apr. 26, 2016

(54) X-RAY IMAGING APPARATUS

(75) Inventor: Kensuke Kobayashi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 444 days.

(21) Appl. No.: 13/230,998

(22) Filed: Sep. 13, 2011

(65) Prior Publication Data

US 2012/0069966 A1 Mar. 22, 2012

(30) Foreign Application Priority Data

Sep. 17, 2010 (JP) ................................. 2010-209990

(51) Int. Cl.
*A61B 6/00* (2006.01)
*G03B 42/04* (2006.01)
*A61B 6/10* (2006.01)

(52) U.S. Cl.
CPC ................. *A61B 6/4283* (2013.01); *A61B 6/00* (2013.01); *A61B 6/56* (2013.01); *G03B 42/04* (2013.01); *A61B 6/10* (2013.01); *A61B 6/4423* (2013.01)

(58) Field of Classification Search
CPC .................................................... A61B 6/4283
See application file for complete search history.

(56) References Cited

U.S. PATENT DOCUMENTS

| | | | |
|---|---|---|---|
| 6,261,715 B1 * | 7/2001 | Nakamura et al. | 429/100 |
| 2008/0240358 A1 * | 10/2008 | Utschig et al. | 378/107 |
| 2008/0311467 A1 * | 12/2008 | Nishimaki et al. | 429/96 |
| 2009/0122959 A1 * | 5/2009 | Jadrich et al. | 378/91 |
| 2010/0165555 A1 * | 7/2010 | Tobiyama et al. | 361/679.01 |
| 2010/0230606 A1 * | 9/2010 | Liu et al. | 250/370.04 |

FOREIGN PATENT DOCUMENTS

| | | | |
|---|---|---|---|
| JP | H09-007567 A | | 1/1997 |
| JP | H09-306451 A | | 11/1997 |
| JP | 11250880 A | | 9/1999 |
| JP | 2002044207 A | | 2/2002 |
| JP | 2002-175791 A | | 6/2002 |
| JP | 2003248060 A | | 9/2003 |
| JP | 2005285713 A | | 10/2005 |
| JP | 2006252825 A | | 9/2006 |
| JP | 2007-059157 A | | 3/2007 |
| JP | 2007-333380 A | | 12/2007 |
| JP | 2009-053661 A | | 3/2009 |

* cited by examiner

*Primary Examiner* — Hoon Song
(74) *Attorney, Agent, or Firm* — Canon U.S.A., Inc. IP Division

(57) ABSTRACT

An X-ray imaging apparatus includes: an X-ray sensor configured to convert an X-ray to an image signal; a battery configured to supply electric power for driving the X-ray sensor; a battery holder configured to detachably hold the battery; a lock mechanism configured to lock the battery in a state in which it is attached to the battery holder; and a lock releasing mechanism configured to release the lock effected by the lock mechanism, wherein the lock releasing mechanism is configured to release the lock by the lock mechanism through at least two operations performed by the operator.

16 Claims, 18 Drawing Sheets

X-RAY IMAGING APPARATUS

BACKGROUND OF THE INVENTION

1. Field of the Invention

The present invention relates to an X-ray imaging apparatus with a detachable battery mounted thereto.

2. Description of the Related Art

X-ray imaging, in which X-rays are applied to a subject to detect the intensity distribution of the X-rays transmitted through the subject to obtain an X-ray image of the subject, is widely utilized in the medical and industrial fields. Historically, the first system for obtaining an X-ray image was using the film-screen method, in which a photosensitive film having captured visible light emitted from an X-ray sensitive rare earth phosphor is chemically developed and visualized. The technological innovations thereafter have produced various systems. Among them is an imaging apparatus (Flat Panel Detector (FPD)) using a planar sensor to which a semiconductor processing technique is applied and in which pixels consisting of minute photoelectric conversion elements and switching elements are arranged in a lattice-like fashion. This apparatus is advantageous in that due to its much larger dynamic range as compared with that of conventional photosensitive films, it can obtain a stable X-ray image even if the X-ray exposure amount fluctuates, and that since it requires no chemical processing, it can quickly obtain an X-ray image.

From the viewpoint of form, the X-ray imaging apparatuses can be classified into an installation-type one that can be installed at a predetermined place such as an ordinary shooting room, and a portable one that can be freely carried about. In recent years, there has been an increasing demand for the portable X-ray imaging apparatus (hereinafter referred to as the "electronic cassette" or just the "cassette.")

In a conventional electronic cassette, a control unit is electrically connected to a cable for supplying power from the outside. Thus, the treatment of the cable is troublesome, which obstructs handling of the electronic cassette; further, a surplus portion of the cable constitutes an obstacle. Further, in a clean (sterilized) environment such as an operation room, it is necessary to prevent the imaging system including the cable from coming into contact with an open (not sterilized) area such as the floor surface.

In view of this, a wireless cassette has recently been developed, in which the power supply cable has been done away with and which contains a battery instead; this novel cassette is expected to achieve a marked improvement of freedom degree in X-ray imagining.

This cassette requires attachment/detachment of the battery in order to perform charging and to replace the battery with a new one; however, when the driving of the cassette cannot be stopped as in the case where an X-ray image is being obtained or in the case where an image is being transferred to a control unit, the attachment/detachment of the battery must be restrained. A pertaining technique is discussed in Japanese Patent Application Laid-Open No. 2007-333380 and Japanese Patent Application Laid-Open No. 2009-53661.

It should be noted, however, that the wireless cassette is to be carried about in use; thus, it is requisite for the battery to be reliably retained even when a shock expected in normal condition of use is received such as vibration or dropping or when the cassette is inserted or drawn into or out of a gap between the subject and the bed. On the other hand, if the frequency of battery attachment/detachment is taken into consideration, it is important, from the viewpoint of improving the feel of use of the cassette, that the lock mechanism requires no special tool, enabling the operator to operate the cassette relatively easily.

SUMMARY OF THE INVENTION

The present invention is directed to an X-ray imaging apparatus allowing releasing of the lock of the battery relatively easily in proper timing while retaining the battery so that it may not be inadvertently detached and fall.

According to an aspect of the present invention, an X-ray imaging apparatus includes an X-ray sensor configured to convert an X-ray to an image signal, a battery configured to supply electric power for driving the X-ray sensor, a battery holder configured to detachably hold the battery, a lock mechanism configured to lock the battery in a state in which it is attached to the battery holder, and a lock releasing mechanism configured to release the lock effected by the lock mechanism, wherein the lock releasing mechanism is configured to release the lock by the lock mechanism through at least two operations performed by an operator.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Figure 1:
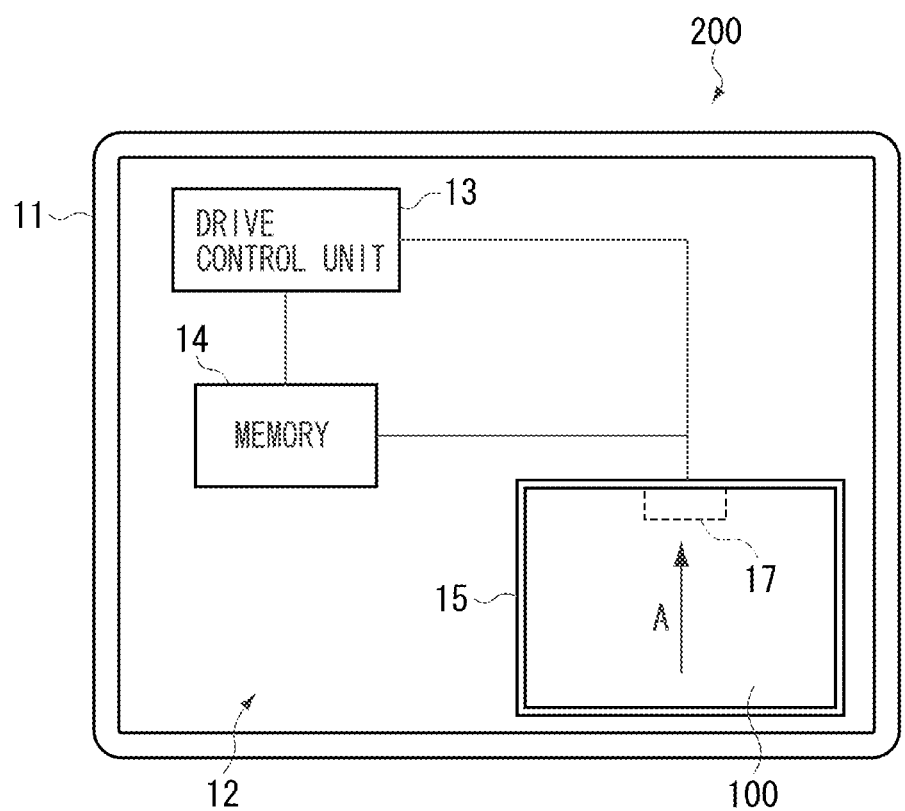
FIG. 1 is a diagram illustrating the construction of an X-ray imaging apparatus according to the present exemplary embodiment.

Various exemplary embodiments, features, and aspects of the invention will be described in detail below with reference to the drawings. The same reference numerals indicate the same or similar parts throughout the drawings.

FIG. 1 is a schematic diagram illustrating a construction common to the X-ray imaging apparatuses according to the first through third exemplary embodiments. An X-ray imaging apparatus 200 includes a casing 11 accommodating an X-ray sensor 12, a drive control unit 13, memory 14, and a battery holder 15. By attaching a battery 100 that has undergone charging, to the battery holder 15, the battery 100 is electrically connected to the X-ray imaging apparatus 200, and supplies electric power to the X-ray sensor 12, the drive control unit 13, and the memory 14 via a holder side connection portion 17.

In FIG. 1, the direction in which the battery 100 is connected to the holder side connection portion 17 is indicated by the arrow A.

Next, an X-ray imaging apparatus 201 according to the first exemplary embodiment will be illustrated with reference to FIGS. 2 through 9.

Figure 2:
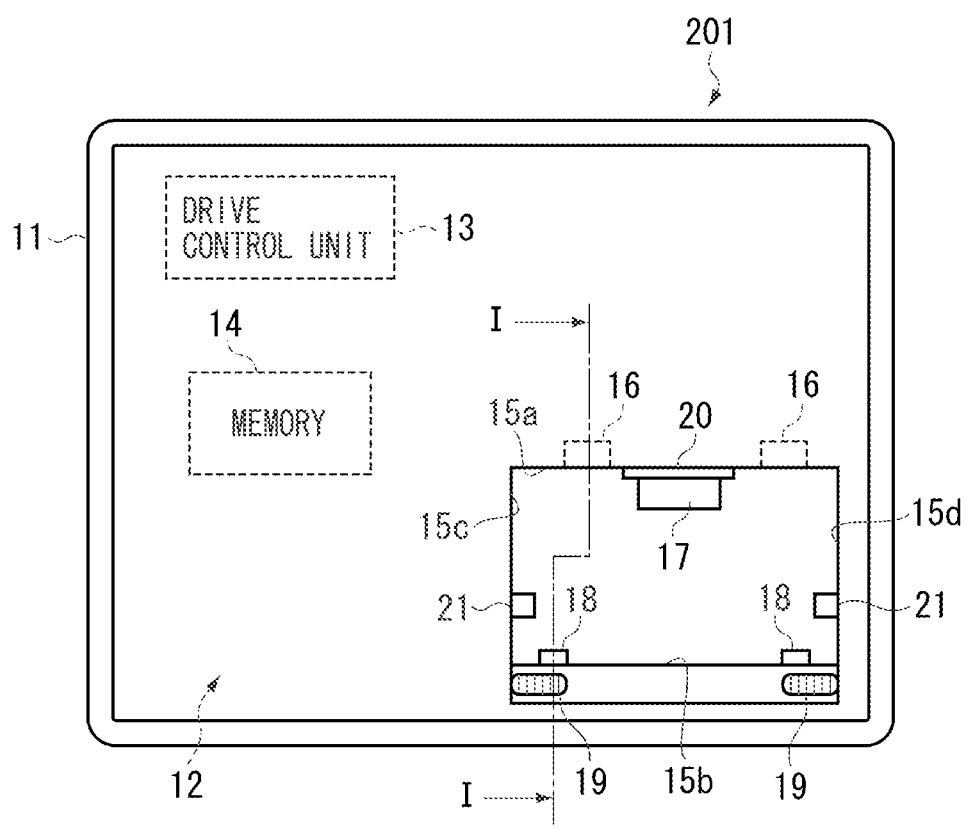
FIG. 2 is a diagram illustrating the construction of an X-ray imaging apparatus according to a first exemplary embodiment with no battery attached thereto.
Figure 3:
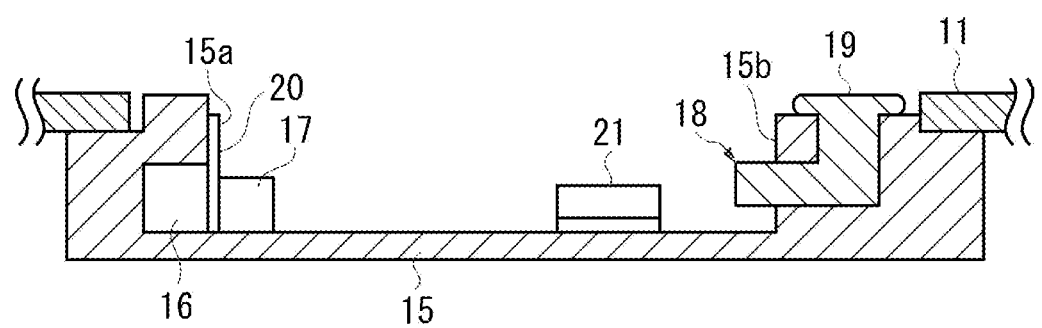
FIG. 3 is a sectional view of the X-ray imaging apparatus with no battery attached thereto.

FIG. 2 is a plan view of the X-ray imaging apparatus with the battery removed from the battery holder. FIG. 2 illustrates the surface on the side opposite the surface where the X-ray sensor 12 is arranged. FIG. 3 is a sectional view taken along the arrow line I-I of FIG. 2.

The battery holder 15 has an inner side surface 15a from which the holder side connection portion 17 protrudes; on the inner side surface 15a and around the holder side connection portion 17, a damper member 20 is provided. The damper member 20 consists, for example, of a thin rubber plate, which is attached to the inner side surface 15a. Further, the inner side surface 15a has, on both sides of the holder side connection portion 17, hole-like insertion guides 16.

On the other hand, on an inner side surface 15b opposite the inner side surface 15a, there are provided battery lock members 18 protruding into the battery holder 15. There are provided two battery lock members 18 separated from each other in the width direction (the horizontal direction in FIG. 2) of the battery holder 15. Each battery lock member 18 has a battery lock operation knob 19 as an operation member that can be operated by the operator; each battery lock operation knob 19 is formed to be exposed on the upper surface of the battery holder 15. The two battery lock members 18 are movable from the positions as shown in FIG. 2 toward each other by a predetermined distance.

Inner side surfaces 15c and 15d adjacent to the inner side surface 15a are respectively provided with pop-up mechanisms 21 in close proximity. The pop-up mechanisms 21 serve to urge the attached battery 100 constantly upwards.

Figure 4A:
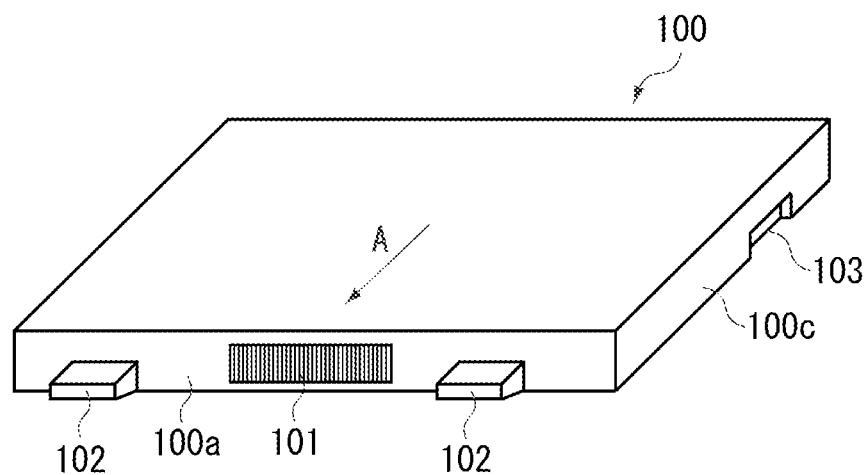
FIGS. 4A and 4B are perspective view illustrating the construction of a battery.
Figure 4B:
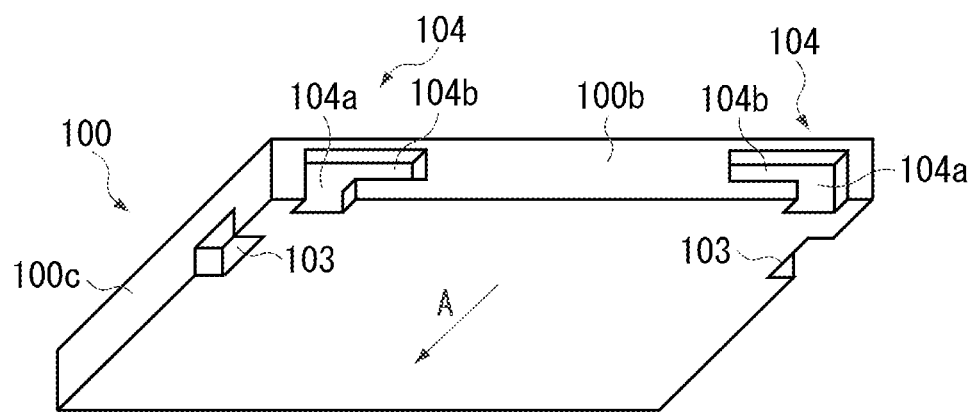

FIG. 4A is a perspective view of the battery as seen from above, and FIG. 4B is a perspective view of the battery as seen from below. In FIGS. 4A and 4B, the direction in which the battery 100 is connected to the holder side connection portion 17 is indicated by the arrow A.

Of the side surfaces of the battery 100, a side surface 100a opposite the inner side surface 15a of the battery holder 15 is provided with a battery terminal 101 that can be connected to the holder side connection portion 17 of the battery holder 15. Further, insertion guides 102 that can be inserted into the insertion guides 16 protrude on both sides of the side surface 100a with the battery terminal 101 therebetween. The insertion guides 102 can determine the inserting direction of the battery 100 to be a predetermined direction. Further, through fit-engagement of the insertion guides 102 and the insertion guides 16, it is possible to suppress rattling of the battery 100 when it is attached to the battery holder 15, and to prevent an excessive load from being applied to the holder side connection portion 17 and the battery terminal 101.

On the other hand, a side surface 100b opposite the side surface 100a has lock recesses 104 that can be engaged with the battery lock members 18. Corresponding to the battery lock members 18, two lock recesses 104 are formed separated from each other in the width direction (the horizontal direction in FIG. 2) of the side surface 102b. The lock recesses 104 respectively have attachment/detachment grooves 104a formed to extend in the vertical direction, and lock grooves 104b formed to extend in the horizontal direction perpendicular to attachment/detachment grooves 104a in close proximity to each other.

A side surface 100c and a side surface 100d that are adjacent to the side surface 100a have, at positions corresponding to the pop-up mechanisms 21 of the battery holder 15, receiving portions 103 to be engaged with the pop-up mechanisms 21.

Next, the operation of attaching the battery 100 to the battery holder 15 will be described.

First, before attaching the battery 100 to the battery holder 15, the operator moves the two battery lock members 18 away from each other as shown in FIG. 2.

Next, the operator inserts the battery 100 into the battery holder 15 in the direction A from above. At this time, the insertion guides 16 guide the insertion guides 102, so that the operator can correctly set the battery 100 in position within the batter holder 15. Further, the operator forces the battery 100 into the battery holder 15, whereby the two battery lock members 18 pass the attachment/detachment grooves 104a of the corresponding lock recesses 104, and the battery 100 is attached to the battery holder 15.

In the state in which the battery 100 has been attached to the battery holder 15, the battery terminal 101 and the holder side connection portion 17 are connected to each other, and the pop-up mechanisms 21 are engaged with the receiving portions 103.

Figure 5:
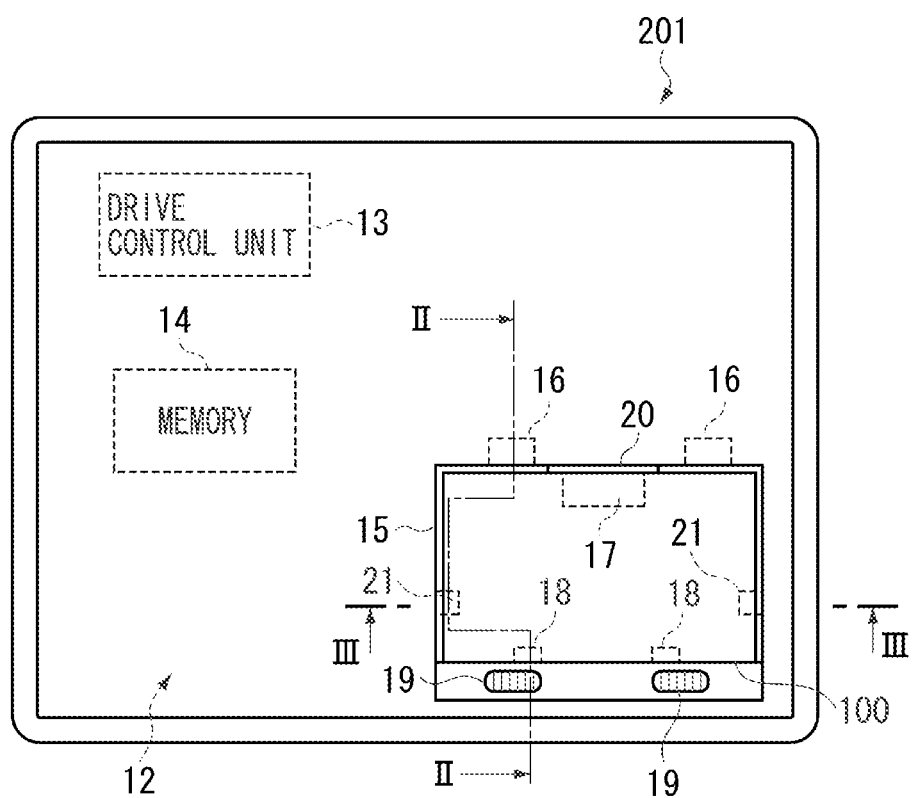
FIG. 5 is a diagram illustrating the construction of an X-ray imaging apparatus with a battery attached thereto.
Figure 6:
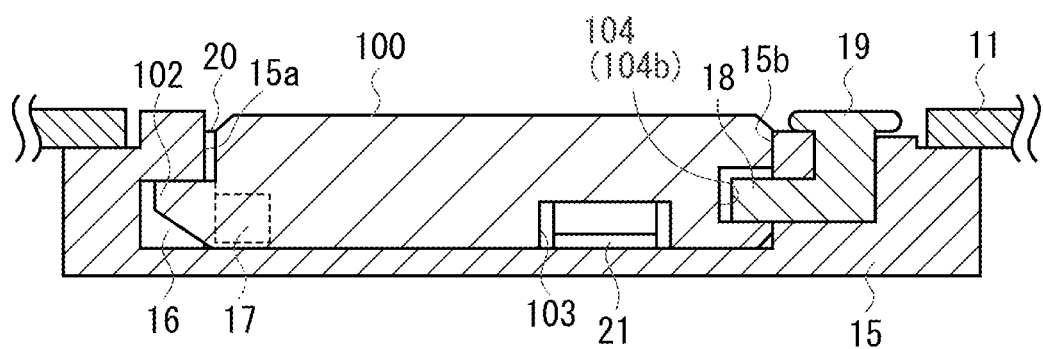
FIG. 6 is a sectional view of the X-ray imaging apparatus when the battery is locked.
Figure 7:
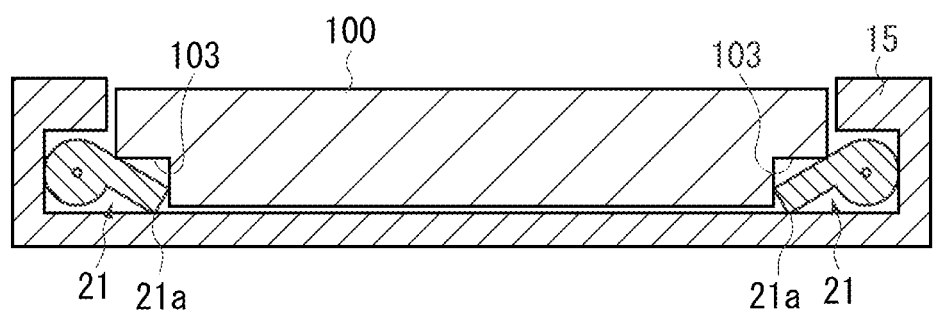
FIG. 7 is a sectional view of the X-ray imaging apparatus when the battery is locked.

FIG. 5 is a plan view of the X-ray imaging apparatus showing the battery 100 as locked to the battery holder 15. FIG. 6 is a sectional view taken along the arrow line II-II of FIG. 5. FIG. 7 is a sectional view taken along the line III-III of FIG. 5.

As illustrated in FIG. 5, after attaching the battery 100 to the battery holder 15, the operator moves the two battery lock knobs 19 toward each other. At this time, as illustrated in FIG. 6, the battery lock members 18 also enter the lock grooves 104b of the corresponding lock recesses 104, with the result that the battery 100 cannot move upwards, so that the battery 100 is locked to the battery holder 15.

In the state in which the battery 100 has been locked to the battery holder 15, the restoring force of the damper member 20 generated through compression by the battery 100 urges the battery 100 toward the inner side surface 15b where the battery lock members 18 are provided. Further, as illustrated in FIG. 7, the pop-up mechanisms 21 have push-up members 21*a* rotatably supported by the battery holder 15. The distal ends of the push-up members 21*a* are urged to rotate upwards by springs (not illustrated). Thus, in the state in which the battery 100 has been locked to the battery holder 15, the restoring force of the pop-up mechanisms 21, which is generated through the pressing of the pop-up mechanisms 21 by the battery 100, upwardly urges the battery 100 via the receiving portions 103. The pop-up mechanisms 21 urge the battery 100 via ridge portions, which excel in strength, so that the main body of the battery 100 is not easily bent.

In this way, the battery 100 is firmly held in the battery holder 15 by urging forces in two different directions, so that it is possible to achieve an improvement in resistance to vibration and shock.

In the case where a material with a sealing property is used for the damper member 20, it is possible to secure the hermeticity around the battery terminal 101 when the battery is attached.

Next, the operation of detaching the battery 100 from the battery holder 15 will be illustrated. When detaching the battery 100, the operator moves the two battery lock operation knobs 19 away from each other. At this time, the battery lock members 18 move from the lock grooves 104*b* to the attachment/detachment grooves 104*a*. Thus, the lock of the battery 100 relative to the battery holder 15 is released, and the battery can move in the vertical direction. Here, the pop-up mechanisms 21 urge the battery 100 upwards via the receiving portions 103, so that, simultaneously with the releasing of its lock, the battery 100 is raised relative to the battery holder 15.

Figure 8:
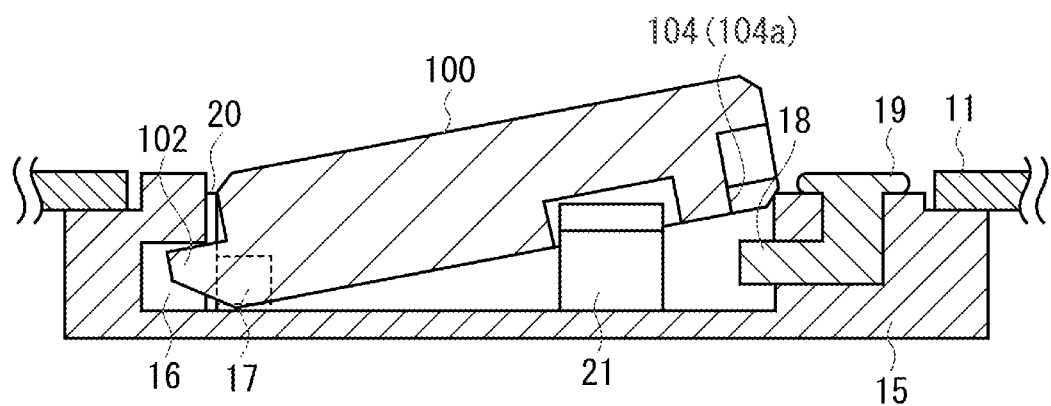
FIG. 8 is a sectional view of the X-ray imaging apparatus when the battery lock is released.
Figure 9:
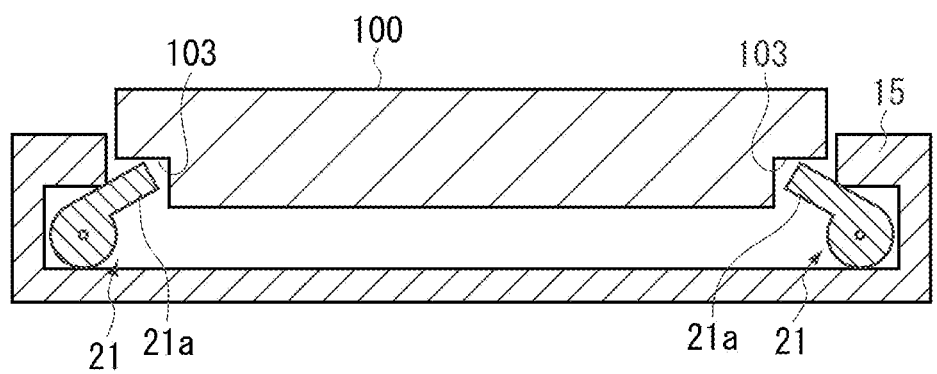
FIG. 9 is a sectional view of the X-ray imaging apparatus when the battery lock is released.

FIGS. 8 and 9 are sectional views illustrating the battery which has been released from the locked state illustrated in FIGS. 6 and 7.

Here, the battery lock members 18, the battery lock operation knobs 19, and the lock recesses 104 of the battery 100 constitute the lock mechanism and the lock releasing mechanism.

In this way, the battery 100, which is firmly held in the battery holder 15, can be easily unlocked by the operator only by moving the battery lock operation knobs 19, making it possible to easily extract the battery 100 from the battery holder 15.

On the other hand, when releasing the lock, it is necessary for the operator to perform the operation of moving the two right and left battery lock operation knobs 19 away from each other, so that it is possible to prevent the lock from being inadvertently released.

The normal driving state for the X-ray sensor 12, which converts an X-ray into an image signal, can, for example, be classified into the following six states:

(1) The unenergized state (sleep state)
(2) The state in which the sensor is energized and a signal from the drive control unit 13 is waited for (before preparation for imaging)
(3) The transition in progress to the state in which imaging is feasible (during preparation for imaging)
(4) The state in which imaging is feasible but no X-ray is being applied
(5) The state in which an X-ray is applied and an image is obtained
(6) The state in which the image signal is stored in the memory 14 after the acquisition of the image Of these, in the states (5) and (6), if the supply of electricity from the battery 100 to the X-ray sensor 12, the drive control unit 13, and the memory 14 is cut off, the image is chipped, and re-imaging is required, which increases the amount by which the subject is exposed to the X-ray. In view of this, a mechanism regulating the releasing of the lock of the battery 100 may be added to the X-ray imaging apparatus described above.

Figure 10:
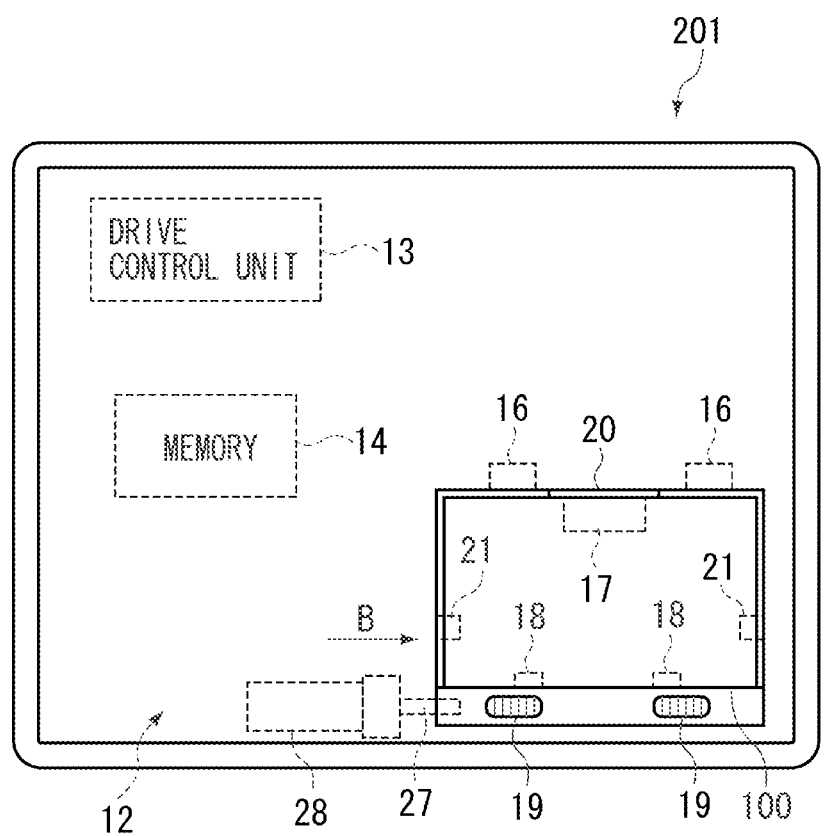
FIG. 10 is a diagram illustrating how the movement of a battery lock member is regulated in the X-ray imaging apparatus.

More specifically, as illustrated in FIG. 10, an X-ray imaging apparatus 201 is equipped with a regulating member 27 capable of intrusion in the direction of the arrow B into the path in which the battery lock members 18 move in order to release the lock of the battery 100. The regulating member 27 is connected to an actuator 28 configured to move in accordance with a command from the drive control unit 13. Thus, the drive control unit 13 causes the regulating member 27 to advance via the actuator 28 so that the supply of electricity to the X-ray sensor 12, the drive control unit 13, and the memory 14 may not be cut off, thereby regulating the operation of the battery lock operation knobs 19 by the operator.

More specifically, as soon as a battery whose remaining power amount is large enough to allow a series of imaging operations is attached, electricity is supplied to the drive control unit 13 and the memory 14. The drive control unit 13 detects this, and causes the regulating member 27 to protrude via the actuator 28.

When the supply of electricity to the X-ray sensor 12, the drive control unit 13, and the memory 14 may be cut off, the drive control unit 13 causes the regulating member 27 to retract via the actuator 28, enabling the operator to operate the battery lock operation knobs 19. Due to this construction, it is possible to prevent erroneous operation by the operator, thus reducing the necessity for re-imaging.

When the remaining power of the battery is short of the requisite amount for imaging, the drive control unit 13 completes the storage of the image in the memory 14 and performs control to prevent preparation for new imaging. Then, it may cause the regulating member 27 to retract via the actuator 28, enabling the operator to operate the battery lock operation knobs 19.

In usual imaging in which center alignment with the X-ray source is made at the center of the X-ray imaging apparatus, the subject is placed on the X-ray imaging apparatus 201, so that a bending load is applied to the X-ray imaging apparatus 201. However, as illustrated in FIG. 2, in the present exemplary embodiment, the battery holder 15 is arranged away from the center of the casing 11, so that it is possible to avoid generation of multi-axis bending in the battery 100.

Further, although in the present exemplary embodiment described above the lock of the battery 100 is released by moving the two right and left battery lock operation knobs 19 away from each other, an exemplary embodiment is not limited to this. For example, it is also possible to release the lock of the battery 100 by moving the two right and left battery lock operation knobs 19 toward each other.

Next, an X-ray imaging apparatus 202 according to the second exemplary embodiment will be illustrated with reference to FIGS. 11 and 12.

Figure 11:
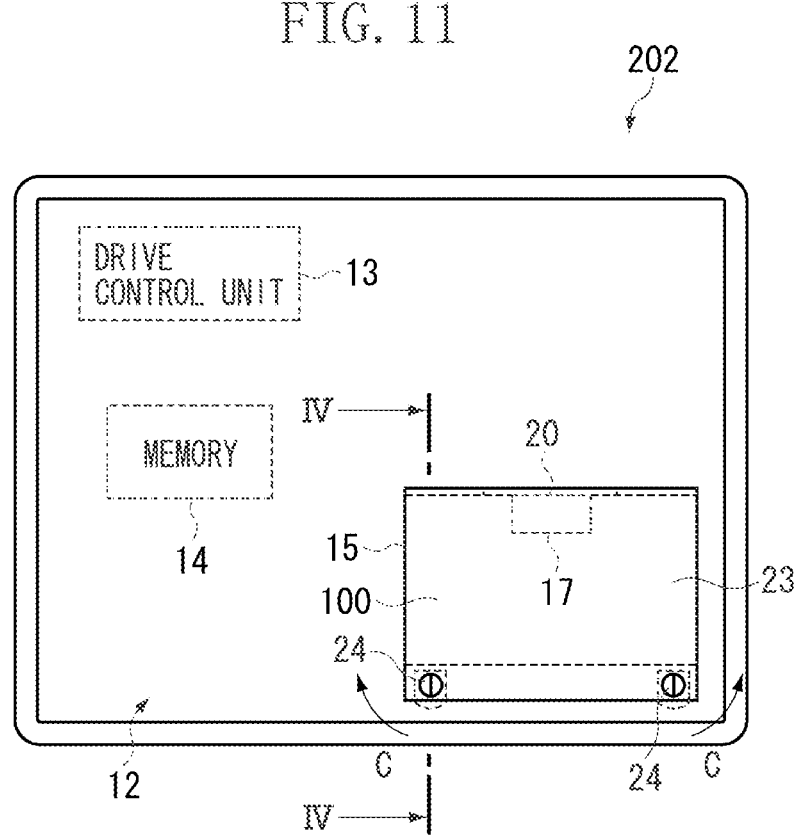
FIG. 11 is a diagram illustrating the construction of an X-ray imaging apparatus according to a second exemplary embodiment with a battery attached thereto.

FIG. 11 is a plan view of the X-ray imaging apparatus in the state in which the battery has been attached to the battery holder. FIG. 12 is a sectional view taken along the arrow line IV-IV of FIG. 11. The components that are similar to those of the first exemplary embodiment are indicated by the same reference numerals, and a description thereof is not repeated.

The battery holder 15 according to the present exemplary embodiment is detachably equipped with a flat battery lock member 23 covering the entire battery 100 from above. At the end portion of one side of the batter lock member 23, there are provided two battery lock operation knobs 24 separated from each other as the operation members that can be operated by the operator. As illustrated in FIG. 12, in the lower portion of each battery lock operation knob 24, a horizontally protruding lock portion 24a is formed. Each battery lock operation knob 24 is rotatable around a vertical axis. By rotating the battery lock operation knobs 24, it is possible to cause the lock portions 24a to protrude from the battery lock member 23.

Figure 12:
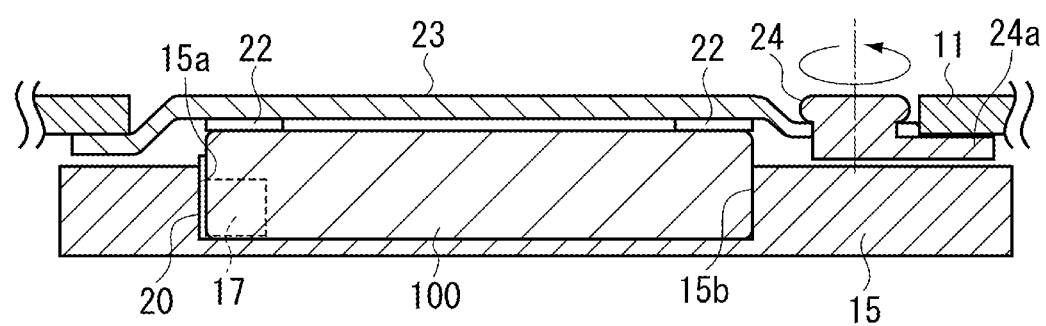
FIG. 12 is a sectional view of the X-ray imaging apparatus when the battery is locked.

As illustrated in FIG. 12, a damper member 22 is provided on the lower surface of the battery lock member 23. The damper member 22 consists, for example, of a thin rubber plate, which is attached to the lower surface of the battery lock member 23.

Next, the operation of attaching the battery 100 to the battery holder 15 will be illustrated.

First, before attaching the battery 100 to the battery holder 15, the operator detaches the battery lock member 23 from the battery holder 23, and rotate the battery lock operation knobs 24 so that the lock portions 24a may not protrude from the battery lock member 23.

Next, the operator inserts the battery 100 into the battery holder 15. After this, the battery lock member 23 is attached to the battery holder 15 to cover the battery 100 from above.

At this time, the operator inserts between the casing 11 and the battery holder 15 the end portion of the side of the battery lock member 23 which is opposite the side where the battery lock operation, knobs 24 are provided. Next, while pushing the battery 100 from above into the battery holder 15 via the battery lock member 23, the operator rotates the two battery lock operation knobs 24. By rotating the battery lock operation knobs 24 and inserting the lock portions 24a into the space between the casing 11 and the battery holder 15, the battery 100 is locked to the battery holder 15. The two battery lock operation knobs 24 are rotated in different directions, whereby the lock portions 24a are respectively inserted into the space between the casing 11 and the battery holder 15.

In the state in which the battery 100 has been locked to the battery holder 15, the damper member 22 attached to the lower surface of the battery lock member 23 is situated to substantially match with the contour ridge of the battery 100. Thus, the restoring force of the damper member 22 generated through compression between the ridge portion of the battery 100 and the battery lock member 23 urges the battery 100 downwards. Further, as in the first exemplary embodiment, the damper member 20 is provided on the inner side surface 15a of the battery holder 15, so that the restoring force of the damper member 20 generated through compression by the battery 100 urges the battery 100 toward the inner side surface 15b. In this way, the battery 100 is firmly held in the battery holder 15 by the urging forces in two different directions, whereby it is possible to achieve sufficient resistance to vibration and shock.

Next, the operation of detaching the battery 100 from the battery holder 15 will be described.

When detaching the battery 100, the operator rotates the two battery lock operation knobs 24 in opposite directions (as indicated by the arrows C in FIG. 11). At this time, the lock portions 24a of the battery lock operation knobs 24 are detached from between the casing 11 and the battery holder 15. Thus, it is possible to detach the battery lock member 23 from the battery holder 15, so that the battery 100 is also unlocked from the battery holder 15.

Here, the battery lock member 23, the battery lock operation knobs 24, the lock portions 24a, and the space between the casing 11 and the battery holder 15 constitute the lock mechanism and the lock releasing mechanism.

In this way, while the battery 100 is firmly held in the battery holder 15, the lock can be easily released only through the operation of moving the battery lock operation knobs 24 by the operator.

On the other hand, to release the lock, it is necessary for the operator to rotate the two right and left lock operation knobs 24 in different directions, so that it is possible to prevent release of lock unintended by the operator. The operation of rotating the two right and left battery lock operation knobs 24 is an operation performed in a fixed state on the rotation axes of the battery lock operation knobs 24, so that it is possible to prevent inadvertent operation more reliably than in the case of sliding operation described with reference to the first exemplary embodiment.

In the construction of the present exemplary embodiment, depending upon the position and size of the lid-like battery lock member 23, it is possible that light outside the casing 11 reaches the X-ray sensor 12, making it impossible to obtain a normal image. Thus, as in the X-ray imaging apparatus illustrated with reference to FIG. 10, at least from the beginning of transition of the X-ray sensor 12 to a state allowing imaging until the completion of image acquisition, the drive control unit 13 may regulate the operation of the battery lock operation knobs 24 by means of a regulating member. By regulating the operation of the battery lock operation knobs 24, it is possible to perform imaging without failure, making it possible to reduce the need for re-imaging.

Next, an X-ray imaging apparatus 203 according to the third exemplary embodiment will be illustrated with reference to FIGS. 13 through 15.

Figure 13:
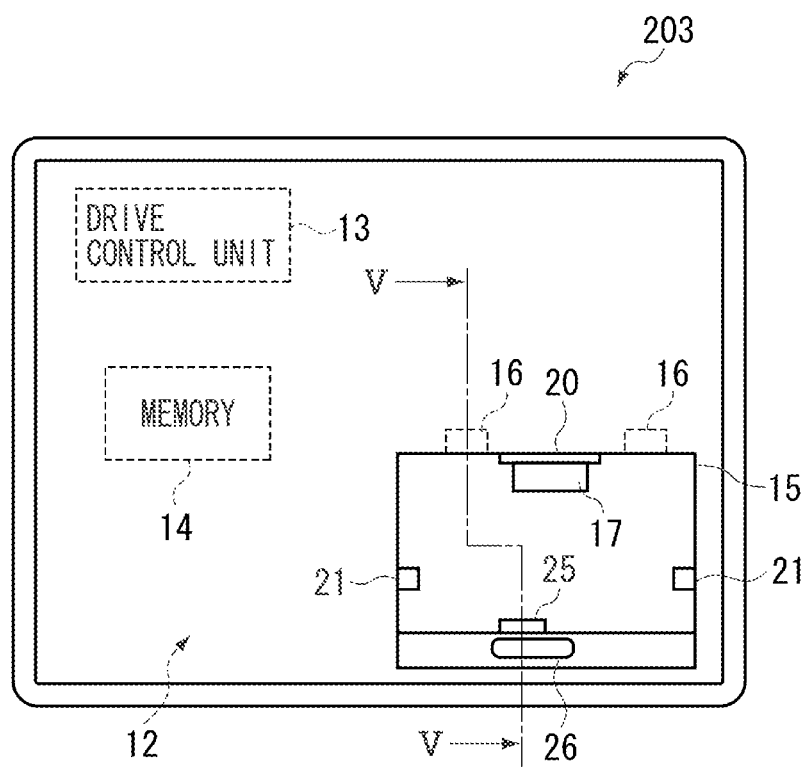
FIG. 13 is a diagram illustrating the construction of an X-ray imaging apparatus according to a third exemplary embodiment with no battery attached thereto.
Figure 14:
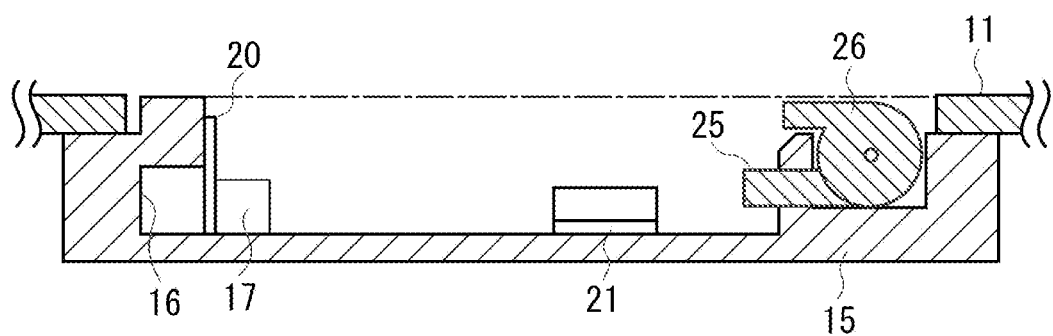
FIG. 14 is a sectional view of the X-ray imaging apparatus when the battery is locked.

FIG. 13 is a plan view of the X-ray imaging apparatus before the attachment of the battery to the battery holder. FIG. 14 is a sectional view taken along the arrow line V-V of FIG. 13. The components that are the same as those of the first exemplary embodiment are indicated by the same reference numerals, and a description thereof is not repeated.

The battery holder 15 of the present exemplary embodiment is provided with one battery lock member 25 as described with reference to the first exemplary embodiment. The battery lock member 25 is provided substantially at the center in the width direction (the horizontal direction in FIG. 13) of the battery holder 15. The battery lock member 25 is movable in the horizontal direction by a predetermined distance from the position as shown in FIG. 13. Further, the battery lock member 25 is provided with a rotatable battery lock operation knob 26 as an operating member that can be operated by the operator.

The rotating operation of the battery lock operation knob 26 relative to the battery lock member 25 will be specifically described with reference to FIG. 15. FIGS. 15A and 15B illustrate the states before and after the rotation of the battery operation knob 26. As illustrated in FIGS. 15A and 15B, the battery lock operation knob 26 is provided to be rotatable around a rotation shaft R relative to the battery lock member 25. In the state illustrated in FIG. 15A, the battery lock operation knob 26 does not protrude from the surface F of the casing 11. In this state, it is difficult for the operator to operate the battery lock operation knob 26 to cause the battery lock member 25 to slide.

Figure 15A:
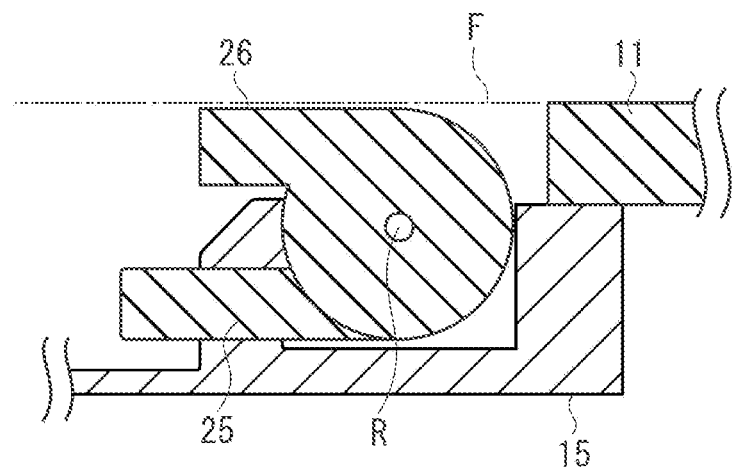
FIGS. 15A and 15B are sectional views illustrating the operation of a battery lock operation knob.
Figure 15B:
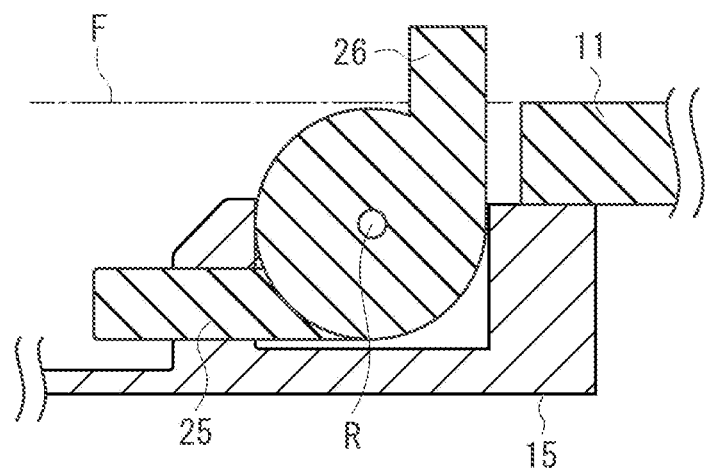

On the other hand, as illustrated in FIG. 15B, in the state in which the batter lock operation knob 26 has been erected through rotation, a part of the battery lock operation knob 26 protrudes from the surface F of the casing 11. In this state, the operator can easily operate the battery lock operation knob 26 to cause the battery lock member 25 to slide.

Thus, when attaching or detaching the battery 100, the operator rotates the battery lock operation knob 26 from the position shown in FIG. 15A to the position shown in FIG. 15B, causing the battery lock member 25 to slide. When there is no need to attach or detach the battery 100, the operator rotates the battery lock operation knob 26 from the position shown in FIG. 15B to the position shown in FIG. 15A so that the battery lock operation knob 26 may not protrude from the surface F of the casing 11.

Here, the battery lock member 25, the battery lock operation knob 26, and the lock recesses 104 of the battery 100 constitute the lock mechanism and the lock releasing mechanism.

In this way, in the normal state of use in which the battery 100 is neither attached nor detached, it is physically difficult for the operator to get to the battery lock operation knob 26. Thus, to release the lock of the battery 100, it is necessary for the operator to perform the two operations, namely rotating the battery lock operation knob 26 to erect it and moving the same in the horizontal direction, so that it is possible to prevent release of lock not intended by the operator. In the present exemplary embodiment, the structure can be made relatively simple as compared with the first and the second exemplary embodiments.

Although in the above-described exemplary embodiment one battery lock member 25 is provided, an exemplary embodiment is not limited to this; it is also possible to provide two or more battery lock members 25. In this case, it is desirable for each battery lock member 25 to be provided with a battery lock operation knob 26 that can change to a state in which operation is feasible and to a state in which operation is not feasible. By increasing the number of provided battery lock members 25, the number of operations required when releasing the lock of the battery 100 increases, so that it is possible to more reliably prevent the battery from being detached inadvertently.

Further, as in the case of the X-ray imaging apparatus illustrated with reference to FIG. 10, also in the present exemplary embodiment, it is also possible to adopt a construction in which the drive control unit 13 regulates the sliding of the battery lock member 25 by a regulating member when the supply of electricity to the X-ray sensor 12, the drive control unit 13, and the memory 14 should no be cut off. In this case, the regulating member may regulate the rotating movement of the battery lock operation knob 26.

The present invention is not restricted to the exemplary embodiments illustrated above but allows modification or the like without departing from the scope of the gist of the invention.

Figure 16:
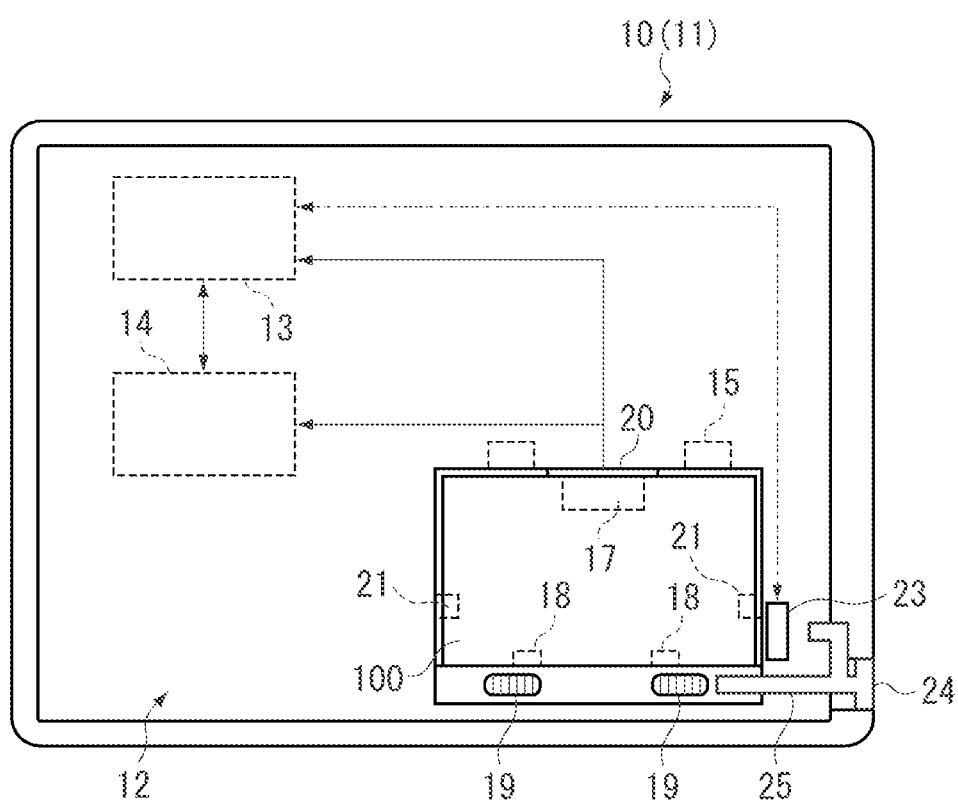
FIG. 16 is a conceptual diagram illustrating an X-ray imaging apparatus according to a fourth exemplary embodiment.

FIG. 16 is a conceptual diagram illustrating a fourth exemplary embodiment of the present invention. In the vicinity of the battery holder 15, a pushbutton type power source switch element 23 is arranged. When a switch operating button 24 is pushed by a certain amount, a switch operating button push bar 25, which is integrated with the switch operating button, pushes the battery lock operation knob 19 in the locking direction, so that the battery lock operation knob 19 is fixed at the lock position.

Figure 17:
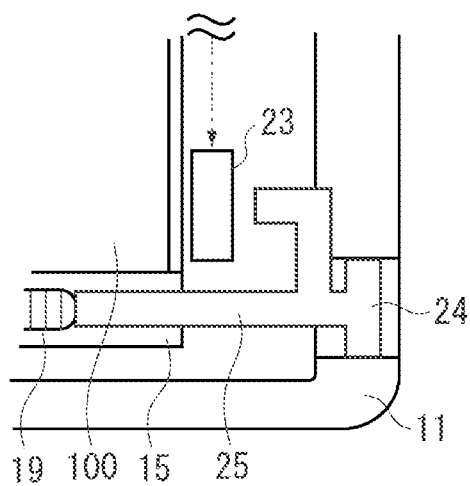
FIG. 17 a schematic diagram (first forcing-in step) illustrating the portion around the battery attachment portion according to the fourth exemplary embodiment.
Figure 18:
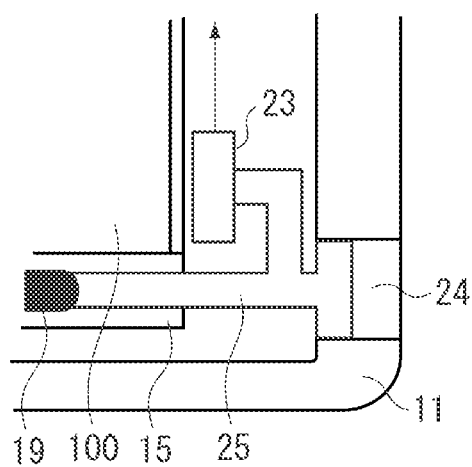
FIG. 18 is a schematic diagram (second forcing-in step) illustrating the portion around the battery attachment portion according to the fourth exemplary embodiment.

FIG. 17 illustrates this fixed state. In this state, the switch operation button push bar 25 has not pushed the power source switch element 23. When, in this state, the switch operation button 24 is further pushed, the switch operation button push bar 25 pushes the power source switch element 23, as shown in FIG. 18, and a signal for placing the power source of the entire electric cassette 10 in the ON state is transmitted to the drive control unit 13. At this time, the switch operation button push bar 25 is fixed by a ratchet mechanism provided in the casing 11, and it is possible to maintain the state in which the battery lock operation knobs 19 have been pushed to the lock positions.

Conversely, to place the power source of the entire electronic cassette 10 in the OFF state, the switch operation button 24 is further pushed lightly; then, the ratchet mechanism operates to release the switch operation button push bar 25. Then, owing to the repulsive force of the a compression spring (not illustrated) provided in the casing 11, the switch operation button 24 and the switch operation button push bar 25 move to the position shown in FIG. 16. In this process, the switch operation button push bar 25 is first separated from the power source switch element 23 (FIG. 17), and then is separated from the battery lock operation knob 19.

In this way, according to the present exemplary embodiment, while the power source switch element 23 is being pushed, in other words, the power source of the entire electronic cassette 10 is in the ON state, the battery lock operation knobs 19 are fixed at the lock positions without fail, so that it is not possible that the electronic cassette 10 is detached, making it possible to perform a stable imaging operation.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2010-209990 filed Sep. 17, 2010, which is hereby incorporated by reference herein in its entirety.

What is claimed is:

1. An X-ray imaging apparatus comprising:
   an X-ray sensor configured to convert incident X-ray radiation into an image signal;
   a battery holder disposed on a second surface of the apparatus opposite to a first surface of the apparatus where the X-ray radiation is incident, the battery holder being configured to detachably hold a battery for supplying electric power to the X-ray sensor;
   a lock mechanism configured to lock the battery in a locked state; and
   a lock releasing unit having a first releasing member and a second releasing member, the lock releasing unit being configured to release the lock effected by the lock mechanism when the first releasing member is moved in a first direction and the second releasing member is moved in a second direction different from the first direction,
   wherein inner surfaces of the battery holder are respectively provided with a first pop-up unit and a second pop-up unit,
   wherein the first pop-up unit and the second pop-up unit are configured to respectively engage with a first receiving portion and a second receiving portion of the battery so as to constantly urge the battery in a vertical direction that is relative and orthogonal to the second surface providing the battery holder,
   wherein the first receiving portion and the second receiving portion are concave shape,
   wherein in the state in which the battery is held to the battery holder, the first pop-up unit and the second pop-up unit are engaged in the first receiving portion and the second receiving portion, and
   wherein the battery holder is disposed away from an edge side surface of the apparatus.

2. The X-ray imaging apparatus according to claim 1, wherein the lock releasing unit releases the lock effected by the lock mechanism so as to change the locked state of the battery to an unlocked state when the first releasing member moves in the first direction and the second releasing member moves in the second direction by a sliding operation or a rotating operation.

3. The X-ray imaging apparatus according to claim 1, wherein the battery holder includes a damper member arranged in close proximity to a connection portion electrically connected to the battery, and
   wherein the damper member is compressed when the battery is in the locked state effected by the locking mechanism.

4. The X-ray imaging apparatus according to claim 1, wherein the first pop-up unit and the second pop-up unit urge the battery in a direction in which the battery is extracted from the battery holder.

5. The X-ray imaging apparatus according to claim 1, further comprising a regulating member configured to regulate an operation of the lock releasing unit according to a driving condition of the X-ray imaging apparatus.

6. The X-ray imaging apparatus according to claim 1, further comprising a power source switch configured to control an operation of the X-ray sensor,
   wherein, while the power source switch controls the operation of the X-ray sensor, the power source switch prevents the lock releasing unit from releasing the lock effected by the lock mechanism through a pressing force of the lock releasing unit.

7. The X-ray imaging apparatus according to claim 1, wherein in the first direction and the second direction are opposite to each other.

8. The X-ray imaging apparatus according to claim 7, wherein the first releasing member moves in the first direction and the second releasing member moves in the second direction away from the first releasing member.

9. The X-ray imaging apparatus according to claim 7, wherein the first releasing member moves in the first direction and the second releasing member moves in the second direction towards the first releasing member.

10. The X-ray imaging apparatus according to claim 7, wherein the first releasing member moves in the first direction and the second releasing member moves in the second direction at the same time.

11. The X-ray imaging apparatus according to claim 1, wherein each of the first releasing member and the second releasing member includes a sliding knob or a rotating knob.

12. The X-ray imaging apparatus according to claim 1, further comprising an actuator configured to prevent the lock releasing unit from releasing the battery from the locked state effected by the lock mechanism,
   wherein the actuator prevents the first releasing member from moving in the first direction and prevents the second releasing member from moving in the second direction.

13. The X-ray imaging apparatus according to claim 1, wherein the lock releasing unit having the first releasing member and the second releasing member is disposed on the side second surface of the apparatus.

14. The X-ray imaging apparatus according to claim 1, further comprising a pop-up mechanism disposed on an inner surface of the battery holder,
   wherein the pop-up mechanism is configured to urge the battery attached to the battery holder in a direction in which the batter is removed from the battery holder.

15. The X-ray imaging apparatus according to claim 14, wherein the battery holder is configured to hold a rectangular battery, and
   wherein the pop-up mechanism is configured to urge a short side of a rectangular battery attached to the battery holder.

16. An X-ray imaging apparatus comprising:
   an X-ray sensor configured to convert incident X-ray radiation into an image signal;
   a battery holder disposed on a second surface of the imaging apparatus opposite to a first surface of the imaging apparatus where the X-ray radiation is incident, the battery holder being configured to detachably hold a battery for supplying electric power to the X-ray sensor;
   a lock mechanism configured to lock the battery in a locked state; and
   a lock-release unit including a first releasing member and a second releasing member, the lock-release unit being configured to release the lock effected by the lock mechanism when the first releasing member is moved in a first direction and the second releasing member is moved in a second direction different from the first direction,
   wherein one or more inner surfaces of the battery holder is provided with a pop-up unit configured to engage with a receiving portion of the battery so as to constantly urge the battery in a vertical direction that is relative and orthogonal to the second surface providing the battery holder, and
   wherein the receiving portion is a concave shape, in the state in which the battery is held to the battery holder, the pop-up unit is engaged in the receiving portion, and
   wherein the battery holder is disposed away from an edge side surface of the X-ray imaging apparatus.

* * * * *